United States Patent [19]

Boden

[11] Patent Number: 4,601,850
[45] Date of Patent: Jul. 22, 1986

[54] 1-HYDROXYMETHYL-2-ISOPROPENYL-1,5-DIMETHYLCYCLOPENTANE, N-PROPYL ESTER THEREOF AND ORGANOLEPTIC USES THEREOF

[75] Inventor: Richard M. Boden, Ocean, N.J.

[73] Assignee: International Flavors & Fragrances Inc., New York, N.Y.

[21] Appl. No.: 685,071

[22] Filed: Dec. 21, 1984

[51] Int. Cl.[4] .............................. A61K 7/46; C11B 9/00
[52] U.S. Cl. ........................... 252/522 R; 252/522 A; 568/579; 568/838
[58] Field of Search .................. 252/522 R; 568/579, 568/838

[56] References Cited

U.S. PATENT DOCUMENTS 4,169,073  9/1979  Mussinan et al. .................. 568/579
4,474,992 10/1984  Licciardello et al. .............. 568/420
4,501,687  2/1985  Martel et al. ..................... 568/838

Primary Examiner—Werren B. Lone
Attorney, Agent, or Firm—Arthur L. Liberman

[57] ABSTRACT

Described are 1-hydroxymethyl-2-isopropenyl-1,5-dimethylcyclopentane and the n-propyl ester thereof defined according to the structure:

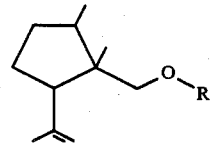

wherein R represents hydrogen or n-propyl. Also described is the use for augmenting or enhancing the aroma of perfumes, colognes and perfumed articles (including solid or liquid anionic, cationic, nonionic or zwitterionic detergents, perfumed polymers, fabric softener compositions, fabric softener articles including drier-added fabric softener articles, hair preparations, cosmetic powders, face creams, moisturizers and the like of the compound having the structure:

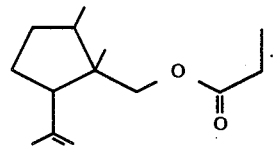

7 Claims, 10 Drawing Figures

GLC PROFILE FOR EXAMPLE I.
CRUDE

GLC PROFILE FOR BULKED FRACTIONS 2-5
OF EXAMPLE I.

FIG.1
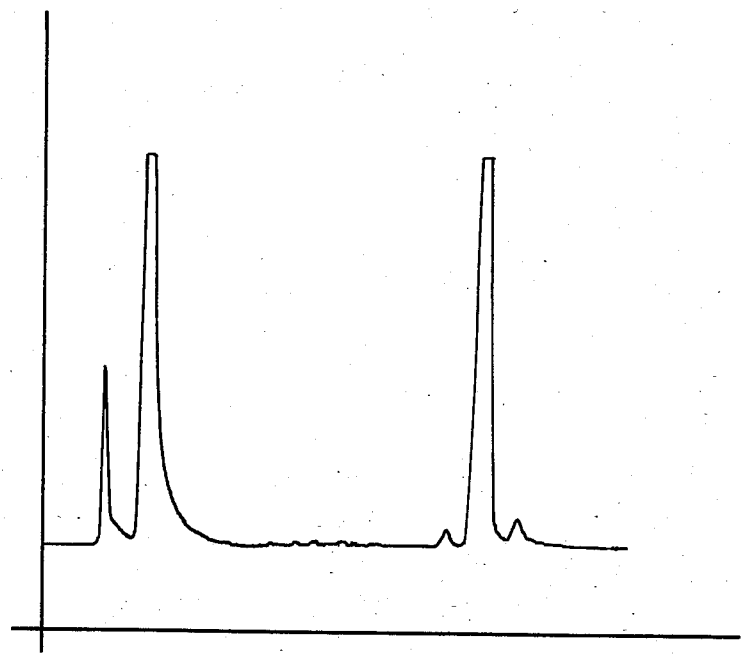
GLC PROFILE FOR EXAMPLE I.
CRUDE
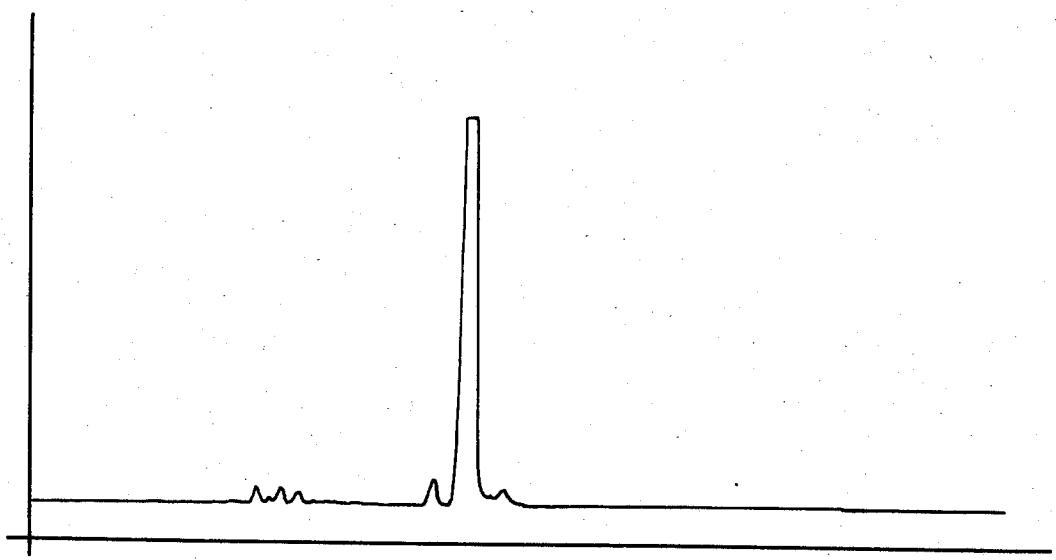
GLC PROFILE FOR BULKED FRACTIONS 2-5
OF EXAMPLE I.
FIG.2

NMR SPECTRUM FOR FRACTION 3 OF EXAMPLE I

IR SPECTRUM FOR FRACTION 3 OF EXAMPLE I.

GLC PROFILE FOR EXAMPLE II.
CRUDE

GLC PROFILE FOR BULKED FRACTIONS 5-7
OF EXAMPLE II.

1-HYDROXYMETHYL-2-ISOPROPENYL-1,5-DIMETHYLCYCLOPENTANE, N-PROPYL ESTER THEREOF AND ORGANOLEPTIC USES THEREOF

BACKGROUND OF THE INVENTION

The present invention provides the novel genus of compounds defined according to the structure:

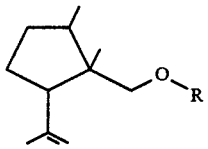

wherein R represents hydrogen or n-propyl and the use of the member of that genus having the structure:

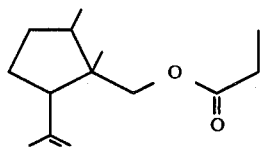

in augmenting or enhancing the aroma of consumable materials.

Materials which can provide rich woody, cedarwood and patchouli aromas with amber topnotes are well known in the art of perfumery. Many of the natural substances which provide such fragrances and contribute the desired nuances to perfumery compositions are high in cost, vary in quality from one batch to another and/or are generally subject to the usual variations of natural products.

The precursor compound of the genus of our invention which precursor is defined according to the structure:

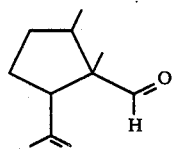

is disclosed for use in augmenting or enhancing the aroma of perfume compositions, colognes and perfumed articles in U.S. Pat. No. 4,474,992 issued on Oct. 2, 1984.

Furthermore, the compound having the structure:

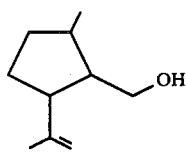

is disclosed (without giving its utilities) by Kaiser and Lamparsky in "Naturliches Vorkommen der Photocitrale und einiger ihrer Derivate", Helv Chim. Acta, Volume 59, Fasc. 5 (1976) No. 184, at page 1797.

The properties of the n-propyl ester of 2-isopropenyl-1,5-dimethylcyclopentane having the structure:

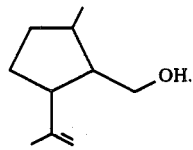

from an organoleptic standpoint are different in kind in an unexpected and advantageous manner from the properties of the compound of the prior art having the structure:

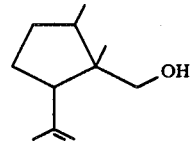

BRIEF DESCRIPTION OF THE DRAWINGS

FIG. 1 is the GLC profile for the crude reaction product produced according to Example I containing the compound having the structure:

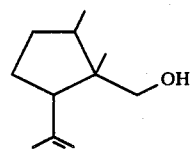

(Conditions: 6'×0.25", 10% carbowax column programmed at 100°-220° C. at 8° C. per minute).

FIG. 2 is the GLC profile for bulked distillation fractions 2-5 of the reaction product of Example I containing the compound having the structure:

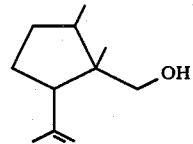

(Conditions: 6'×0.25", 10% carbowax column programmed at 100°-220° C. at 8° C. per minute).

Figure 3:
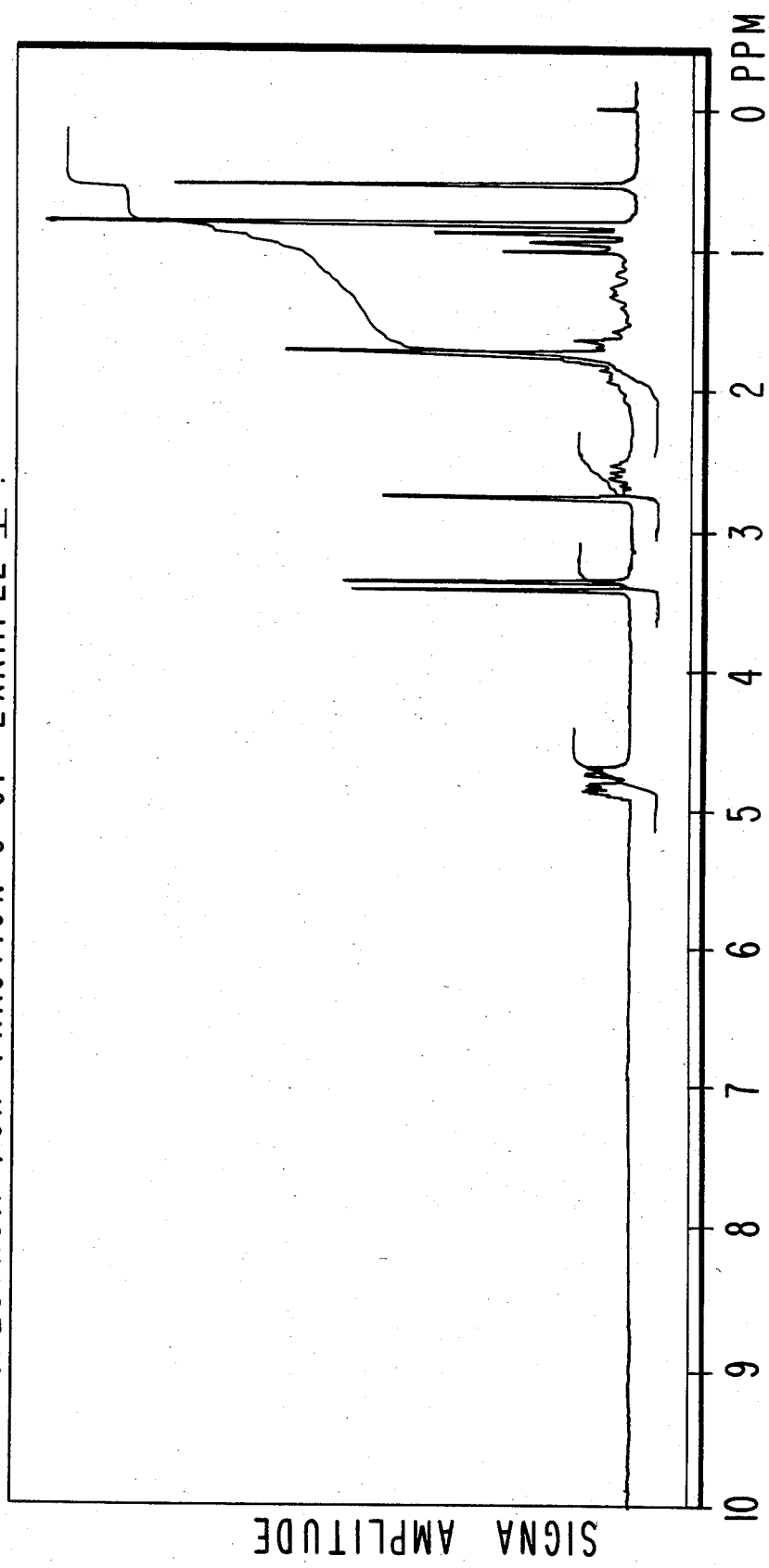

FIG. 3 is the NMR spectrum for fraction 3 of the distillation of the reaction product of Example I containing the compound having the structure:

(Conditions: Field strength: 100 MHz; Solvent: CFCl₃).

Figure 4:
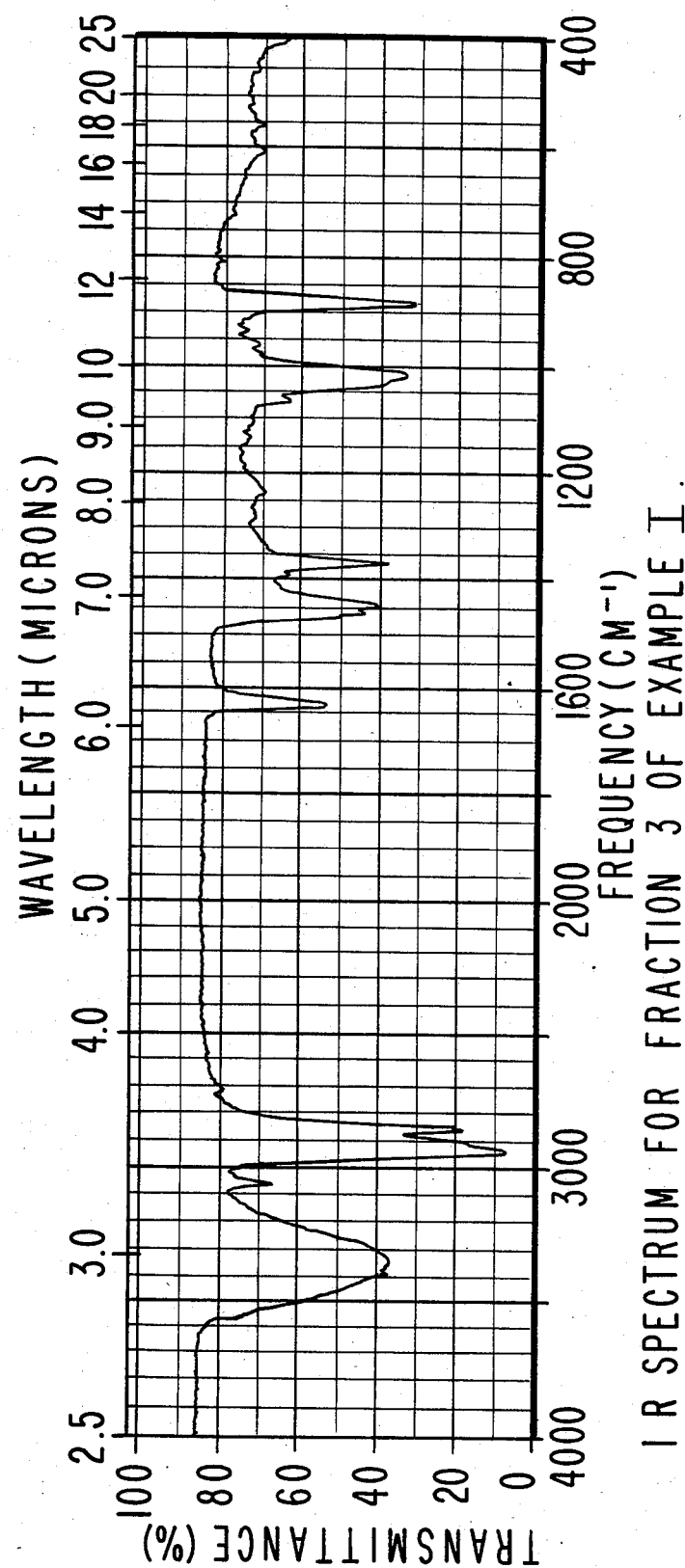

FIG. 4 is the infra-red spectrum for fraction 3 of the distillation product of the reaction product of Example I containing the compound having the structure:

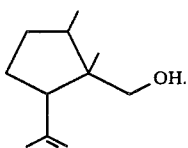

Figure 5:
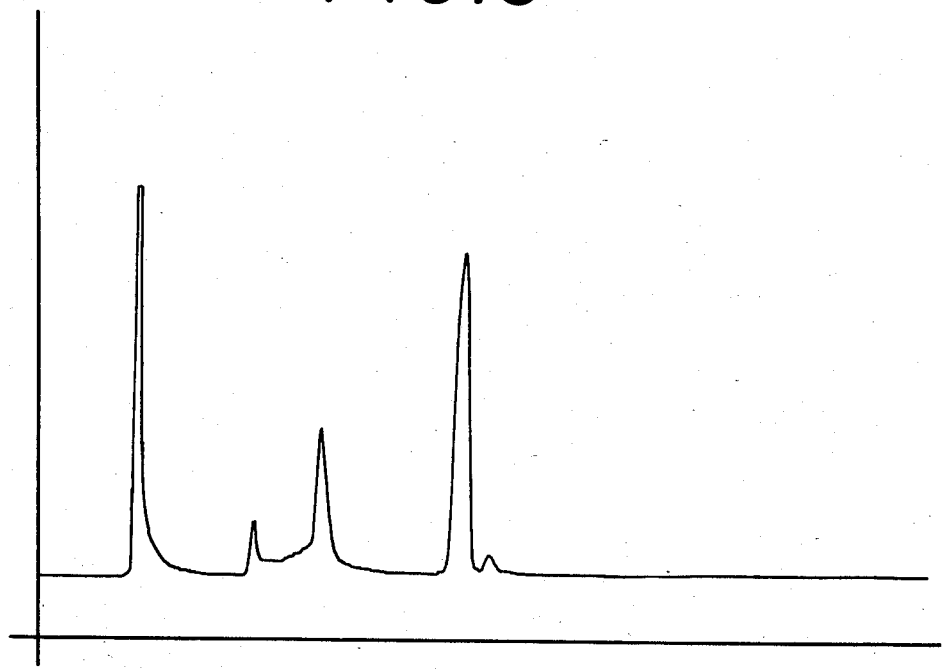

FIG. 5 is the GLC profile for the crude reaction product of Example II containing the compound having the structure:

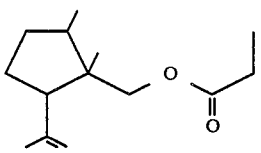

(Conditions: 6'×0.25", 10% carbowax column programmed at 100°-220° C. at 8° C. per minute).

Figure 6:
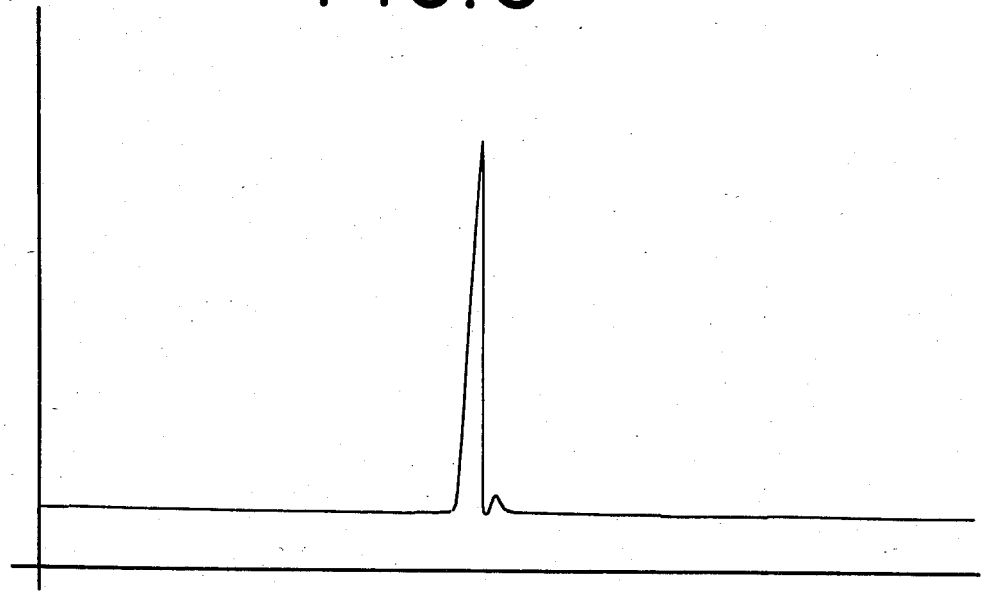

FIG. 6 is the GLC profile for bulked fractions 5-7 of the distillation of the reaction product of Example II containing the compound having the structure:

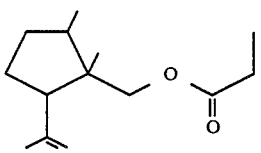

(Conditions: 6'×0.25", 10% carbowax column programmed at 100°-220° C. at 8° C. per minute).

Figure 7:
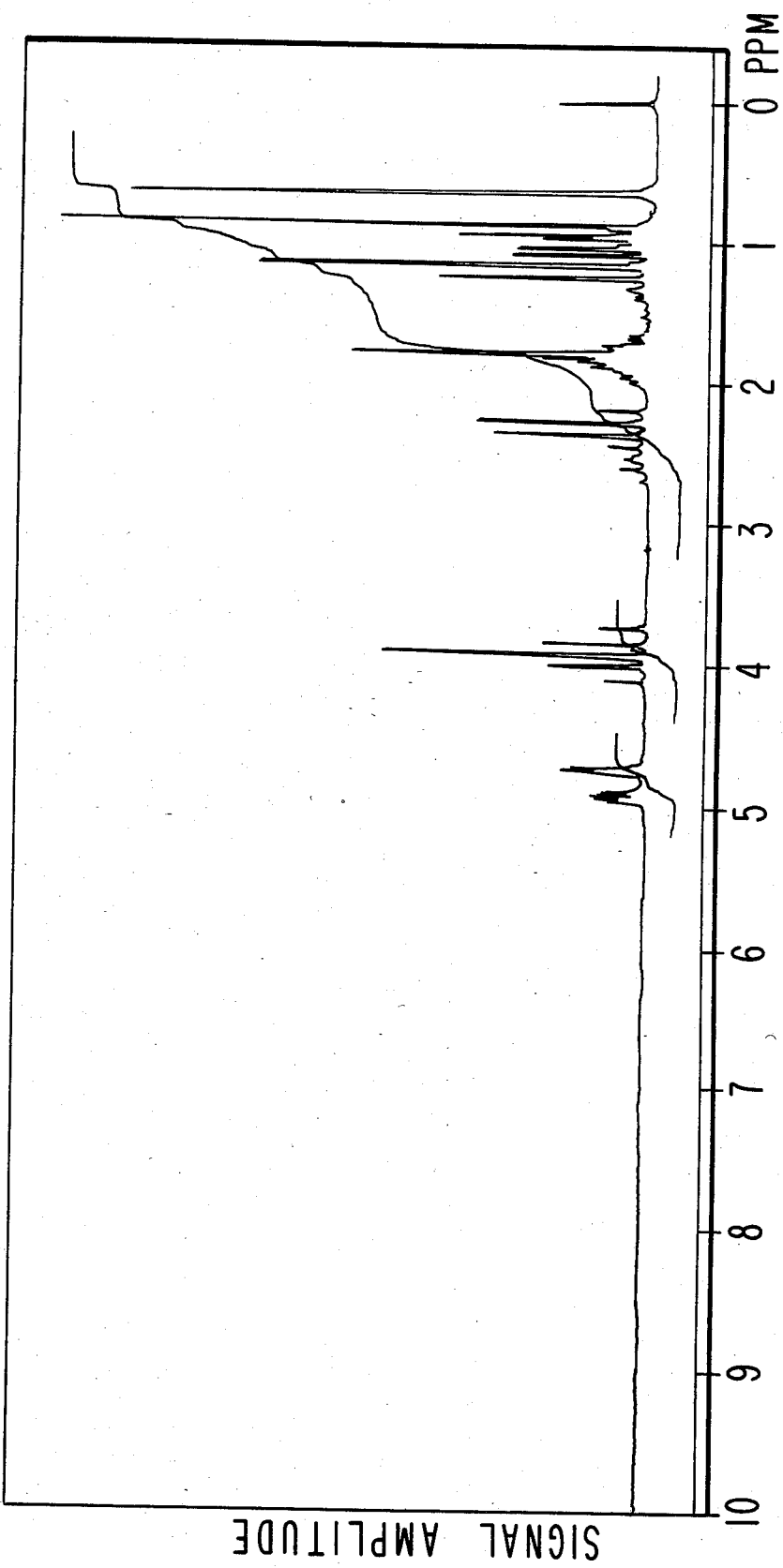

FIG. 7 is the NMR spectrumm for the compound having the structure:

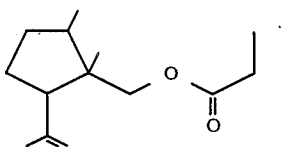

prepared according to Example II (Conditions: Field strength: 100 MHz; Solvent: CFCl₃).

Figure 8:
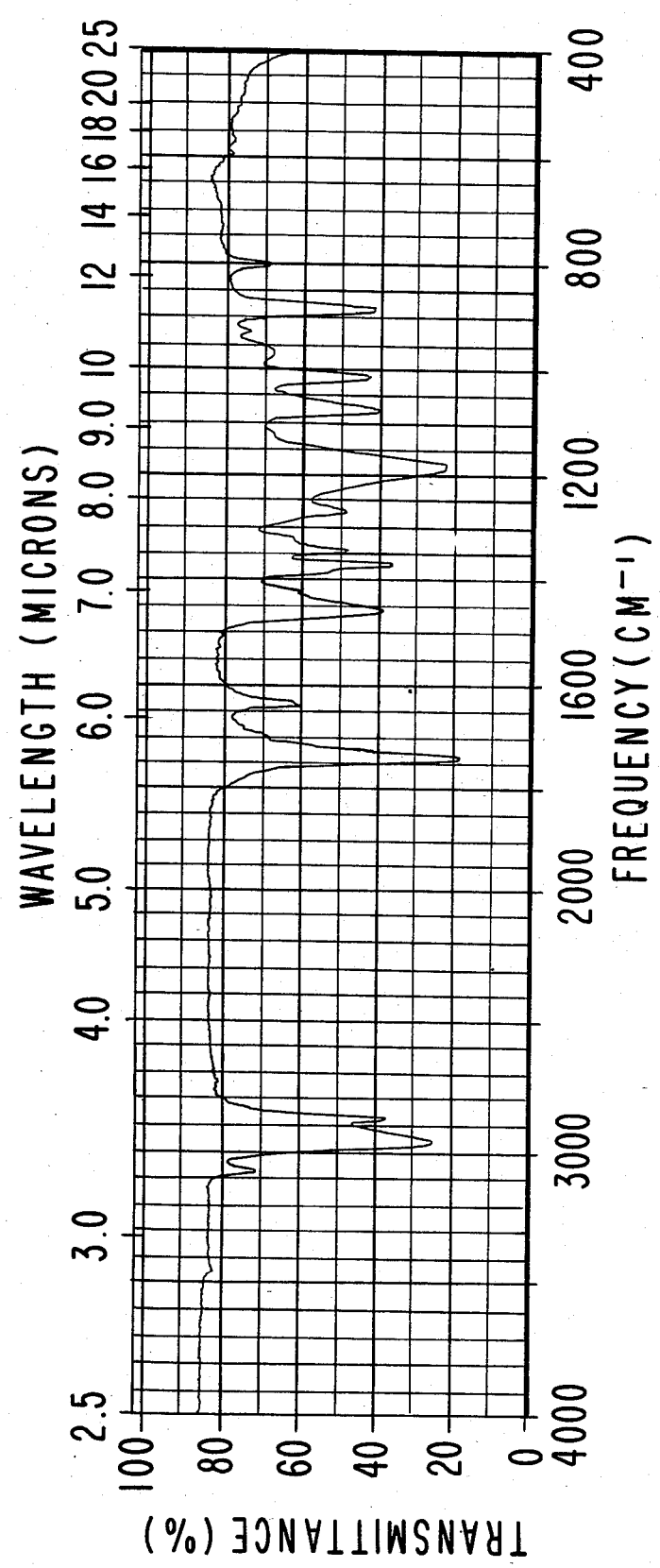

FIG. 8 is the infra-red spectrum for the compound having the structure:

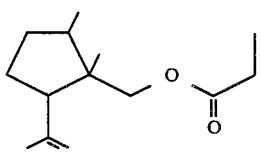

prepared according to Example II.

Figure 9:
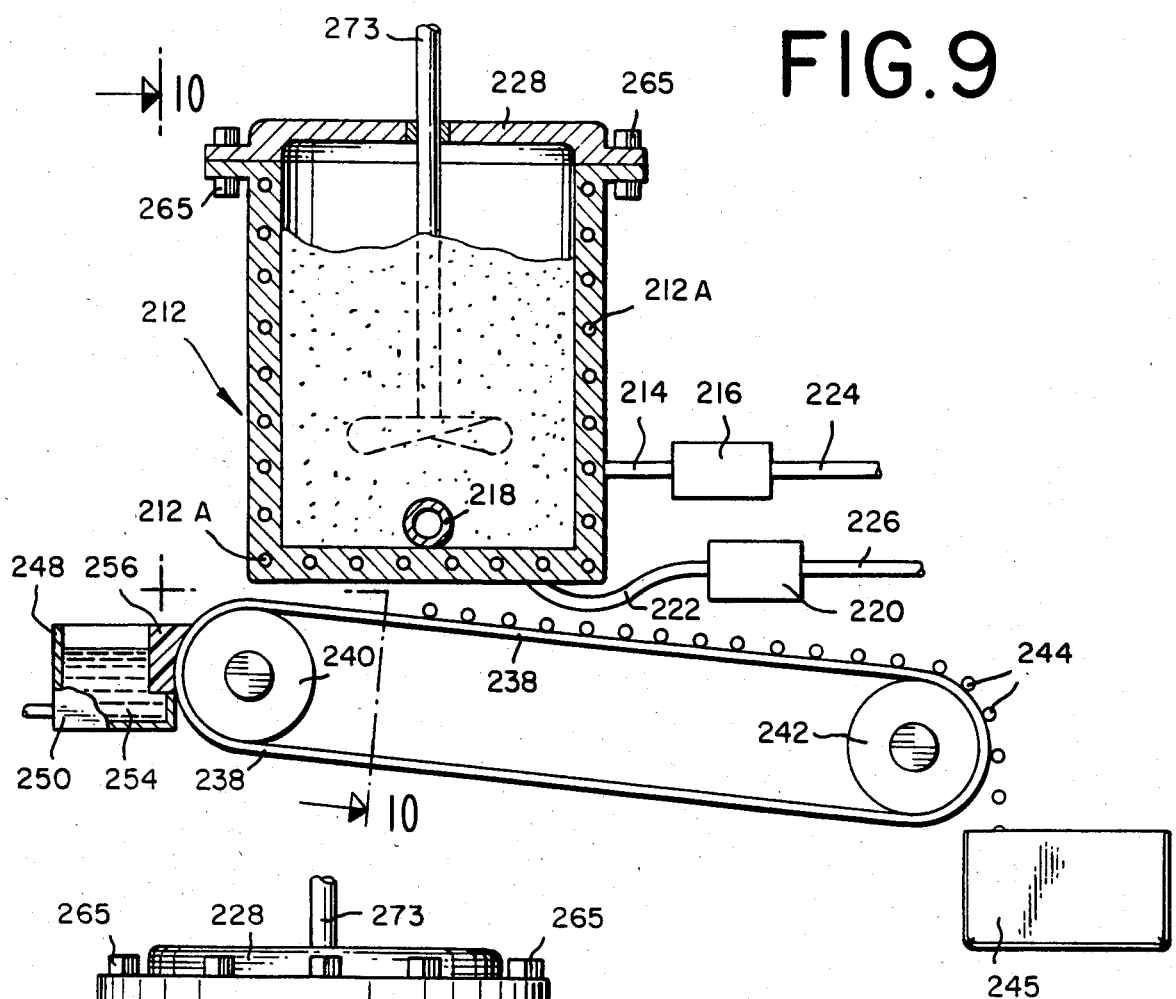

FIG. 9 is a cut-away side elevation view of apparatus used in preparing the perfume substance-containing polymers of our invention.

Figure 10:
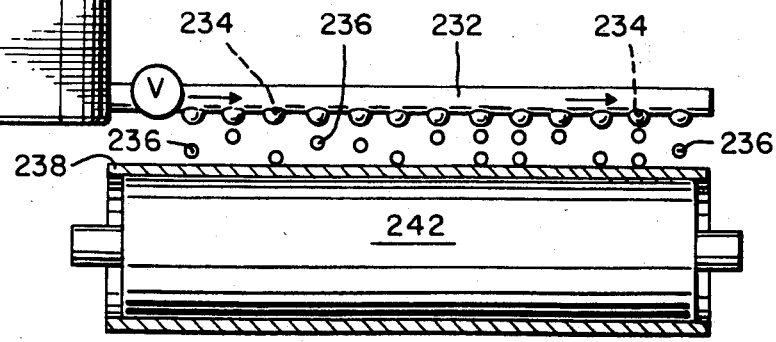

FIG. 10 is a cross-sectional view taken along lines 10—10 of FIG. 9.

DETAILED DESCRIPTION OF THE DRAWINGS

FIGS. 9 and 10 illustrate a preferred method for preparing compositions for the practice of our invention. A thermoplastic polymer, e.g., polyethylene is heated to about 220°-250° F. in a container 212 of the kind illustrated in FIGS. 9 and 10. A formulation containing at least the n-propyl ester of 2-isopropenyl-1,5-dimethylcyclopentane and, if desired, other perfumery materials is then quickly added to the liquified thermoplastic polymer. The lid 228 is put in place and the agitating means 273 is actuated. The temperature is maintained at about 225° F. and the mixing is continued for about 5-15 minutes. The valve "V" is then opened to allow flow of the molten thermoplastic polymer enriched with fragrance to exit through the orifices 234. The liquid falling through the orifices 234 solidifies almost instantaneously upon impact with moving cooled conveyor 238. The thermoplastic polymer beads or pellets having pronounced fragrances (when containing the n-propyl ester of 2-isopropenyl-1,5-dimethylcyclopentane having "rich woody, cedarwood, patchouli aromas with amber topnotes") are thus formed.

The conveyor 238 is moved using conveyor rollers 240 and 242. The vessel 212 is heated using heating coils 212A powered using power input supplies indicated by reference numerals 214, 216, 224, 222, 220 and 226. The solidified beads containing the n-propyl ester of 2-isopropenyl-1,5-dimethylcyclopentane are indicated by reference numeral 244 to be travelling into container 245 where they are used for subsequent processing. The conveyor is cooled using a cooling device indicated by reference numerals 248, 256, 250 and 254.

THE INVENTION

The present invention provides the genus defined according to the structure:

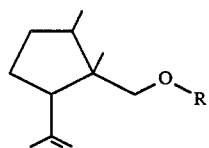

wherein R represents n-propyl or hydrogen and the member of that genus having the structure:

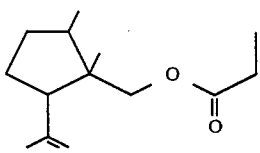

useful in augmenting or enhancing the aroma of perfume compositions, perfumed articles and colognes.

The compound having the structure:

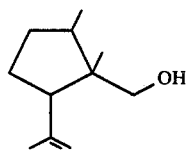

of our invention may be prepared by reducing the compound having the structure:

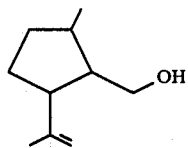

using an alkali metal hydride reducing agent, e.g., sodium borohydride according to the reaction:

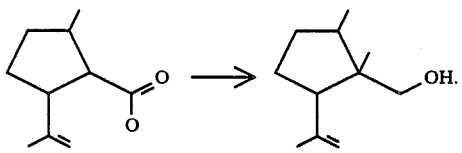

The reaction is carried out at reflux conditions at a temperature of between about 60° C. and about 100° C. using an inert solvent having a boiling point consistent with the desired reflux conditions and time of reaction. Operative inert solvents are isopropyl alcohol and ethyl alcohol. The weight ratio of alkali metal metal hydride to the n-propyl ester of 2-isopropenyl-1,5-dimethylcyclopentane may vary from about 1:10 down to about 1:5. The concentration of the n-propyl ester of 2-isopropenyl-1,5-dimethylcyclopentane in the solvent may vary from about 10 weight percent up to about 50 weight percent. When carrying out the reaction using an isopropyl alcohol solvent a reaction time of between about 3 hours and about 6 hours is preferred. At the end of the reaction, the reaction mass is washed with water and sodium chloride solution and then extracted with toluene. The toluene extract is then distilled on a short path column followed by a careful fractional distillation.

The reaction product is then reacted with propionic anhydride using standard esterification conditions, that is, in the presence of a solvent capable of causing the reaction to be carried out at reflux at a temperature of between about 100° C. and 120° C., e.g., toluene according to the reaction:

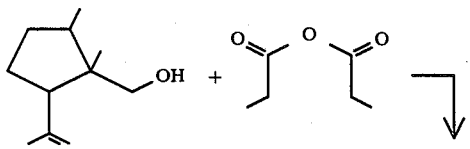

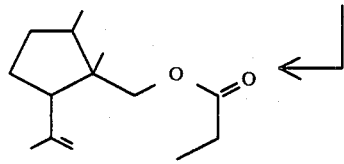

A preferred reaction time for this reaction is between about 10 hours and about 20 hours.

At the end of the reaction the reaction mass is worked up by washing same with water followed by sodium carbonate followed by aqueous sodium chloride. The reaction mass is then carefully fractionally distilled yielding the n-propyl ester of 2-isopropenyl-1,5-dimethylcyclopentane having the structure:

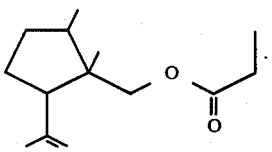

The precursor compound having the structure:

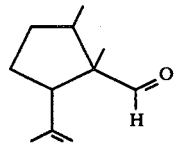

is prepared according to the procedures set forth in U.S. Pat. No. 4,474,992 issued on Oct. 2, 1984 the specification for which is incorporated by reference herein.

The n-propyl ester of 2-isopropenyl-1,5-dimethylcyclopentane of our invention can be used to contribute rich woody, cedarwood, patchouli aromas with amber topnotes to perfume compositions, colognes and perfumed articles such as solid or liquid anionic, cationic, nonionic or zwitterionic detergents, perfume polymers, fabric softener compositions, fabric softener articles, optical brighteners, fabric conditioners, hair preparations, shampoos and hair sprays. As an olfactory agent the n-propyl ester of 2-isopropenyl-1,5-dimethylcyclopentane of our invention can be formulated into or used as a component of a "perfume composition".

The term "perfume composition" is used herein to mean a mixture of organic compounds including, for example, alcohols, aldehydes, ketones, nitriles, ethers, lactones, esters other than the ester of our invention and frequently hydrocarbons which are admixed so that the combined odors of the individual components produce a pleasant or desired fragrance. Such perfume compositions usually contain:

(a) the main note or the "bouquet" or foundation stone of the composition;
(b) modifiers which round off and accompany the main note;
(c) fixatives which include odorous substances which lend a particular note to the perfume throughout all stages of evaporation and substances which retard evaporation; and
(d) topnotes which are usually low-boiling, fresh-smelling materials.

In perfume compositions the individual component will contribute its particular olfactory characteristics, but the overall effect of the perfume composition will be the sum of each of the effects of each of the ingredients. Thus, the n-propyl ester of 2-isopropenyl-1,5-dimethylcyclopentane of this invention can be used to alter the aroma characteristics of the perfume composition, for example, by highlighting or moderating the olfactory reaction contributed by another ingredient in the composition. The amount of the n-propyl ester of 2-isopropenyl-1,5-dimethylcyclopentane of our invention which will be effective in perfume compositions depends upon many factors including the other ingredients, their amounts and the effects which are desired. It has been found that perfume compositions containing as little as 0.1 percent of the n-propyl ester of 2-isopropenyl-1,5-dimethylcyclopentane of our invention or even less in perfume compositions containing as much as 70 percent of the n-propyl ester of 2-isopropenyl-1,5-dimethylcyclopentane of our invention can be used to impart, augment or enhance interesting rich roody, cedarwood, patchouli aromas with amber topnotes in perfumed articles, perfume compositions and colognes. Such perfumed articles include fabric softener compositions, drier-added fabric softener articles, cosmetic powders, talcs, solid or liquid anionic, cationic, nonionic or zwitterionic detergents and perfumed polymers. The amount employed can range up to 70 percent and will depend upon considerations of cost, nature of the end product and the effect desired on the finished product and particular fragrance sought.

Thus, the n-propyl ester of 2-isopropenyl-1,5-dimethylcyclopentane of our invention can be used alone or in a perfume composition as an olfactory component, in solid or liquid anionic, cationic, nonionic or zwitterionic detergents (including hand soaps), perfume polymers (those which may be microporous and those which are macroporous and may contain, if desired, particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer or a polymer containing an absorbent filler or a perfumed article such as a solid or liquid cationic, anionic, nonionic or zwitterionic detergent or a cosmetic powder, as little as 0.01 percent of the n-propyl ester of 2-isopropenyl-1,5-dimethylcyclopentane of our invention will suffice to provide an interesting rich woody, cedarwood, patchouli aroma with amber topnotes. Generally, no more than 0.8 percent of the n-propyl ester of 2-isopropenyl-1,5-dimethylcyclopentane of our invention is required in a perfumed article. Accordingly, the range of the n-propyl ester of 2-isopropenyl-1,5-dimethylcyclopentane in perfumed articles for the purposes of our invention is from about 0.01 percent up to about 0.8 percent.

In addition, the perfume composition of our invention can contain a vehicle or a carrier for the n-propyl ester of 2-isopropenyl-1,5-dimethylcyclopentane of our invention alone or with other ingredients. The vehicle can be a liquid such as an alcohol such as ethanol, a glycol such a propylene glycol or the like. The carrier can be an absorbent solid such as gum (e.g., xanthan gum, gum arabic or guar gum) or components for encapsulating the composition as by coacervation (using gelatine) or by forming a polymer around a liquid center, e.g., using a urea formaldehyde prepolymer to form a polymeric wall around a liquid perfume center.

When incorporating the n-propyl ester of 2-isopropenyl-1,5-dimethylcyclopentane of our invention into polymers, various techniques well known to those skilled in the art may be used. Thus, the n-propyl ester of 2-isopropenyl-1,5-dimethylpentane of our invention may be admixed with amolten polymer such as polyethylene or polypropylene and the resulting mixture may be formed into pellets which are used as a polymer concentrate. In the alternative, the n-propyl ester of 2-isopropenyl-1,5-dimethylpentane of our invention taken alone or taken further in combination with other perfume ingredients may be blended into a polymer during an extrusion operation using a single screw or twin screw extruder. When using an extruder, polymers of ethylene, propylene, ethylene/vinyl acetate copolymers and poly(epsilon caprolactone) as well as various nylons, e.g., nylon-6 may be used.

The following example Example I sets forth the process for preparing the precursor alcohol for the n-propyl ester of 2-isopropenyl-1,5-dimethylcyclopentane of our invention. Example II sets forth the process for preparing the n-propyl ester of 2-isopropenyl-1,5-dimethylcyclopentane of our invention. Example III, et seq. represents methods for using the n-propyl ester of 2-isopropenyl-1,5-dimethylcyclopentane of our invention for its organoleptic properties.

Unless otherwise indicated, all parts and percentages are by weight.

EXAMPLE I

Preparation of 2-isopropenyl-1,5-dimethylcyclopentanemethanol

Reaction:

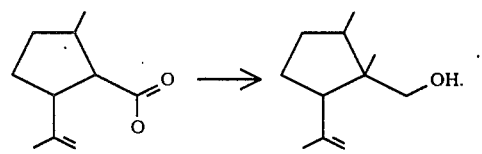

Into a 250 ml flask equipped with stirrer, thermometer reflux condensor, heating mantle and nitrogen blanket apparatus are placed 15 grams of sodium borohydride, 100 ml anhydrous isopropyl alcohol and 65 grams of 2-isopropenyl-1,5-dimethylcyclopentane carboxaldehyde having the structure:

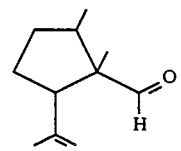

prepared according to U.S. Pat. No. 4,474,992 issued on Oct. 2, 1984.

Under a nitrogen blanket, the reaction mass is refluxed with stirring for a period of four hours. At the end of the four hour period, the reaction mass is washed with 1 liter of water. 25 Ml of toluene is added and the reaction mass is then washed with 1 liter of water. Another 25 ml of toluene is added and the reaction mass is washed with 1 liter of a saturated sodium chloride solution.

The reaction mass is then distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 45 | 93 | 2.0 |
| 2 | 87 | 95 | 2.0 |
| 3 | 87 | 105 | 2.0 |
| 4 | 90 | 150 | 2.0 |
| 5 | 80 | 220 | 2.0 |

FIG. 1 is the GLC profile for the crude reaction product prior to distillation (conditions: 6'×0.25" 10% carbowax column programmed at 100°–220° C. at 8° C. per minute.

FIG. 2 is the GLC profile for bulked distillation fractions 2–5 of the foregoing distillation (conditions: 6'×0.25" 10% carbowax column programmed at 100°–220° C. at 8° C. per minute).

FIG. 3 is the NMR spectrum for fraction 3 of the foregoing distillation containing the compound having the structure:

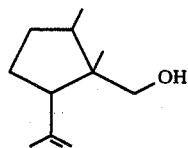

(conditions: Field strength: 100 MHz; Solvent: CFCl$_3$).

FIG. 4 is the infra-red spectrum for fraction 3 of the foregoing distillation containing the compound having the structure:

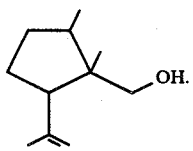

EXAMPLE II

Preparation of Propionic Acid Ester of 2-Isopropenyl-1,5-Dimethylcyclopentanemethanol Reaction:

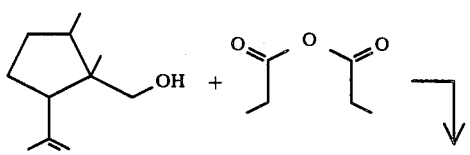

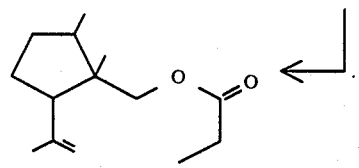

Into a 250 cc reaction flask equipped with stirrer, thermometer, reflux condensor and heating mantle is placed 120 ml toluene and 68 grams of propionic anhydride. The resulting mixture is heated to 100° C. with stirring. Over a period of 15 minutes 0.24 moles (40 grams) of the compound having the structure:

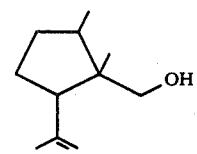

prepared according to Example I is added to the reaction mass. The reaction mass is refluxed at 115° C. for a period of 15 hours. At the end of the 15 hour period, the reaction mass is washed with water followed by one volume of aqueous saturated sodium bicarbonate followed by one volume of aqueous saturated sodium chloride solution. The reaction mass is then distilled on a micro distillation column yielding the following fractions:

| Fraction No. | Vapor Temp. (°C.) | Liquid Temp. (°C.) | Vacuum mm/Hg. Pressure |
|---|---|---|---|
| 1 | 62 | 98 | 14.0 |
| 2 | 35 | 94 | 3.0 |
| 3 | 98 | 109 | 3.0 |
| 4 | 100 | 110 | 3.0 |
| 5 | 100 | 111 | 3.0 |
| 6 | 100 | 112 | 3.0 |
| 7 | 100 | 120 | 3.0 |
| 8 | 100 | 165 | 3.0 |
| 9 | 96 | 210 | 3.0 |

Bulked fractions 3–9 have an interesting very intense rich woody, cedarwood, patchouli aroma with amber topnotes.

FIG. 5 is the GLC profile for the crude reaction product containing the compound having the structure:

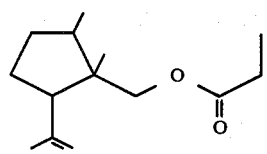

(conditions: 6'×0.25" 10% carbowax column programmed at 100°–220° C. at 8° C. per minute).

FIG. 6 is the GLC profile for bulked fractions 5–7 of the reaction product containing the compound having the structure:

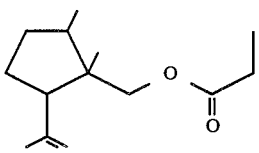

(conditions: 6'×0.25" 10% carbowax column programmed at 100°–220° C. at 8° C. per minute).

FIG. 7 is the NMR spectrum for the compound having the structure:

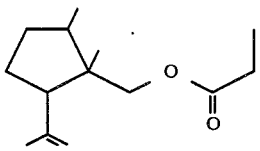

(conditions: Field strength: 100 MHz; Solvent: CFCl$_3$).

FIG. 8 is the infra-red spectrum for the compound having the structure:

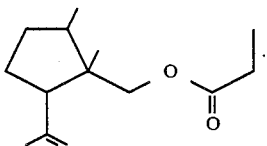

EXAMPLE III

Tropical Forest Fragrance Formulation

| Ingredients | Parts by Weight |
|---|---|
| Amyl cinnamic aldehyde | 20.0 |
| Phenyl acetaldehyde dimethyl acetal | 4.0 |
| Thyme oil white | 8.0 |
| Sauge sclaree French | 8.0 |
| Galbanum oil | 4.0 |
| Juniper berry oil | 10.0 |
| Methyl octin carbonate | 4.0 |
| Linalyl acetate | 2.0 |
| Patchouli alcohol | 12.0 |
| Dihydro methyl jasmonate | 10.0 |
| The compound having the structure: | 15.0 |

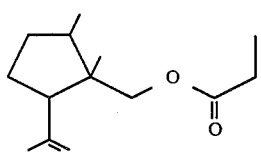

prepared according to Example II, bulked fractions 5–7.

The compound having the structure:

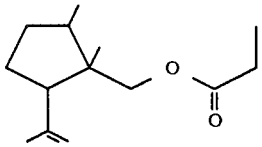

imparts to this tropical forest fragrance formulation a rich woody, cedarwood, patchouli undertone profile with amber topnotes. Accordingly, the fragrance can be described as "tropical forest-like with rich woody, cedarwood, patchouli undertones and amber topnotes".

EXAMPLE IV

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| The compound having the structure:<br><br>prepared according to Example II, bulked fractions 5–7. | A rich woody, cedarwood, patchouli aroma with amber topnotes. |
| The perfume composition of Example III. | A tropical forest-like with rich woody, cedarwood, patchouli undertones and amber topnotes. |

EXAMPLE V

Preparation of Colognes and Handkerchief Perfumes

Compositions as set forth in Table I of Example IV are incorporated into colognes at concentrations of 2.0%, 2.5%, 3.0%, 3.5%, 4.0% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VI

Preparation of Soap Compositions

One hundred trams of soap chips (per sample) (IVORY ® produced by the Procter & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VII

Preparation of Solid Detergent Compositions

Detergents are prepared using the following ingredients according to Example I of Canadian Pat. No. 1,007,948 (incorporated by reference herein):

| Ingredient | Percent by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substrates of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example IV, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y. in 91.62 grams of 95% of food grade ethanol. 8.0 Grams of the polymer is dissolved in the alcohol. The following ingredients are added to the PVP/VA alcoholic solution:

| | |
| --- | --- |
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example IV. | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

EXAMPLE XI

Impregnated Plastics and Air Freshener

Scented polyethylene pellets having pronounced aromas as set forth in Table I of Example IV are prepared as follows:

75 Pounds of polyethylene having a melting point of about 220° F. is heated to about 230° F. in a container of the kind illustrated in FIGS. 9 and 10. 12.5 Pounds of one of the aroma substances of Table I of Example IV, supra are then quickly added, separately, to the liquified polyethylene. The lid 228 is put in place and the agitating means 273 is actuated. The temperature is maintained at about 225° F. and the mixing is continued for about 15 minutes. The valve "V" is then opened to allow flow of the molten polyethylene enriched with the aroma substance of Table I of Example IV through the orifices 234 (whereby such material exits through the orifices 234). The liquid falling through the orifices 234 solidifies almost instantaneously upon impact with the moving cooled conveyor 238. Polyethylene beads or pellets 224 having aromas as set forth in Table I of Example IV are thus formed. These pellets may be called "master pellets".

50 Pounds of the aromatized "master pellets" are then added to 1000 pounds of unscented and untreated polyethylene powder and the mass is heated to the liquid state. The liquid is molded into thin sheets or films. The thin sheets or films have pronounced aromas as set forth in Table I of Example IV. The sheets or films are cut into strips ¼" in width × 3" in length and employed in standard air freshening apparatus.

On operation of the standard air freshening apparatus as a room air freshener, after 4 minutes the room has an aesthetically pleasing aroma as set forth in Table I of Example IV.

EXAMPLE XII

Treated Plastics and Air Freshener

100 Pounds of polypropylene are heated to about 300° F. 15 Pounds of one of the fragrance materials of Table I of Example IV are then added to the liquified polypropylene. The procedure is carried out in the apparatus shown in FIGS. 9 and 10. After mixing for about 8 minutes, the valve "V" is opened to allow the exit of the polypropylene mixture which has been treated with one of the fragrance substances of Table I of Example IV whereby solid pellets having aromas as set forth in Table I of Example IV are formed on the conveyor. The pellets thus obtained are then admixed with about 20 times their weight of unscented polypropylene and a mixture is heated and molded into "spaghetti" tows. The spaghetti tows are cut into small cylinders approximately 0.1" in length × 0.2" in diameter. The cylinders have strong and pleasant aromas as set forth in Table I of Example IV.

The cylinders are used in standard air freshening apparatus to produce aesthetically pleasing aromas as set forth in Table I of Example IV in the air surrounding the air freshening apparatus.

A portion of the cylinders are ground into small particles to be used in the deodorant stick of Example XIII and, for example, XIII, deodorant stick.

A deodorant stick composition is prepared containing the following materials:

| Ingredients | Parts by Weight |
|---|---|
| Propylene Glycol | 65.00 |
| Sodium Stearate | 7.00 |
| Distilled Water | 23.75 |
| IRGASAN ® DP-300 2,4,4-trichloro-2'-hydroxy diphenyl ether manufactured by the Ciba-Geigy Chemical Co. and a Trademark of the Ciba-Geigy Chemical Co.) | 0.25 |
| Ground Polymer containing fragrance prepared according to Example XII, supra | 4.00 |

The ingredients are combined without the ground polymer and heated to 75° C. These ingredients are mixed and continued to be heated until the sodium stearate has dissolved. The resulting mixture is cooled to 40° C. and the ground polymeric substance containing fragrance (one of the materials of Table I of Example IV, supra) is added and mixed at 40° C. until a suspension is formed. The suspension is cooled to room temperature and formed into sticks. On use the sticks impart to the user a pleasant fragrance as set forth in Table I of Example IV.

What is claimed is:

1. The compound having the structure:

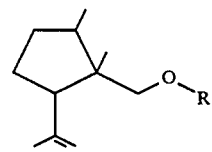

wherein R represents hydrogen or n-propyl.

2. The compound of claim 1 wherein R is hydrogen.
3. The compound of claim 1 wherein R is n-propyl.
4. A process for augmenting or enhancing the aroma of a consumable material selected from the group consisting of perfume compositions, colognes, perfumed polymers and perfumed articles comprising the step of intimately admixing with said consumable material an aroma augmenting or enhancing quantity of the compound of claim 3.
5. The process of claim 4 wherein the consumable material is a perfume composition, cologne or perfumed polymer.
6. The process of claim 4 wherein the consumable material is a perfumed article and the perfumed article is a solid or liquid anionic, cationic, nonionic or zwitterionic detergent.
7. The process of claim 4 wherein the consumable material is a perfumed article and the perfumed article is a fabric softener composition or fabric softener article.

* * * * *